(12) United States Patent
Riley et al.

(10) Patent No.: US 11,393,021 B1
(45) Date of Patent: Jul. 19, 2022

(54) APPARATUSES AND METHODS FOR RESPONSIVE FINANCIAL TRANSACTIONS

(71) Applicant: Wells Fargo Bank, N.A., San Francisco, CA (US)

(72) Inventors: Emma Riley, San Francisco, CA (US); Nichole Runge, San Francisco, CA (US); Riley Warren Hughes, Webster Groves, MO (US); Tabitha Brett, San Francisco, CA (US); Kristina Johnson, San Francisco, CA (US); Jacob Colliflower, Belleville, IL (US); Jonathan Paul Sidarous, House Springs, MO (US); Nicholas K. Pieri, Worden, IL (US)

(73) Assignee: Wells Fargo Bank, N.A., San Francisco, CA (US)

( * ) Notice: Subject to any disclaimer, the term of this patent is extended or adjusted under 35 U.S.C. 154(b) by 0 days.

(21) Appl. No.: 16/900,231

(22) Filed: Jun. 12, 2020

(51) Int. Cl.
  *G06Q 40/02* (2012.01)
  *G06Q 20/10* (2012.01)
  *G16H 40/67* (2018.01)
  *G06Q 50/26* (2012.01)

(52) U.S. Cl.
  CPC .......... *G06Q 40/02* (2013.01); *G06Q 20/108* (2013.01); *G06Q 50/265* (2013.01); *G16H 40/67* (2018.01)

(58) Field of Classification Search
  USPC .......................................................... 705/42
  See application file for complete search history.

(56) References Cited

U.S. PATENT DOCUMENTS

| | | | | |
|---|---|---|---|---|
| 8,260,634 B1 * | 9/2012 | Lawlor | .................. | G06Q 10/10 705/2 |
| 8,447,627 B1 * | 5/2013 | Cruise | .................... | G06Q 40/08 705/2 |
| 8,811,951 B1 * | 8/2014 | Faaborg | ................ | H04W 12/06 455/418 |
| 9,507,325 B1 * | 11/2016 | Barrie | .................... | G04G 21/04 |
| 10,073,953 B2 * | 9/2018 | Xing | .................... | G06Q 20/322 |
| 10,817,891 B1 * | 10/2020 | Hakimi-Boushehri | ...................... | G07C 5/0841 |

(Continued)

OTHER PUBLICATIONS

P. C. Mondal, R. Deb and M. N. Huda, "Transaction authorization from Know Your Customer (KYC) information in online banking," 2016 9th International Conference on Electrical and Computer Engineering (ICECE), 2016, pp. 523-526,(KYC) (Year: 2016).*

(Continued)

*Primary Examiner* — Chikaodinaka Ojiaku
(74) *Attorney, Agent, or Firm* — Womble Bond Dickinson (US) LLP

(57) ABSTRACT

Apparatuses, methods, and computer program products are provided for responsive transactions. An example method includes receiving device data of a first user device associated with a first user and determining a critical event of the first user based upon the device data. The method further includes acquiring financial profile parameters of a first user profile associated with the first user and generating a responsive financial transaction based upon the critical event and the financial profile parameters. The method also include effectuating the responsive financial transaction and/or generate a user notification that includes the responsive financial transaction.

20 Claims, 5 Drawing Sheets

(56) References Cited

U.S. PATENT DOCUMENTS

| | | | | |
|---|---|---|---|---|
| 2007/0027714 | A1* | 2/2007 | Fenno | G16H 40/20 705/2 |
| 2007/0168234 | A1* | 7/2007 | Rutkowski | G06Q 40/08 705/4 |
| 2007/0198432 | A1* | 8/2007 | Pitroda | G06Q 20/325 705/64 |
| 2008/0010203 | A1* | 1/2008 | Grant | H04L 67/2828 705/44 |
| 2008/0167990 | A1* | 7/2008 | Grant | H04L 67/2828 705/44 |
| 2009/0063192 | A1* | 3/2009 | Giles | G16H 40/63 705/3 |
| 2009/0069642 | A1* | 3/2009 | Gao | H04L 67/125 600/300 |
| 2011/0106698 | A1* | 5/2011 | Isaacson | G06Q 30/02 705/41 |
| 2012/0150732 | A1* | 6/2012 | Isaacson | G06Q 20/384 705/39 |
| 2012/0150743 | A1* | 6/2012 | Isaacson | G06Q 30/06 705/41 |
| 2012/0179577 | A1* | 7/2012 | Isaacson | G06Q 30/0613 705/26.41 |
| 2013/0046688 | A1* | 2/2013 | Grant | G06Q 40/02 705/40 |
| 2013/0090940 | A1* | 4/2013 | Goodnight | G06Q 10/10 705/2 |
| 2013/0151433 | A1* | 6/2013 | Hicks | G06Q 30/0279 705/329 |
| 2013/0176142 | A1* | 7/2013 | Drysdale | G16H 20/30 340/870.02 |
| 2013/0290427 | A1* | 10/2013 | Proud | H02J 50/90 709/204 |
| 2013/0304486 | A1* | 11/2013 | Jagemann | G06Q 10/10 705/2 |
| 2014/0052567 | A1* | 2/2014 | Bhardwaj | G06Q 30/0631 705/26.7 |
| 2014/0073969 | A1* | 3/2014 | Zou | A61B 5/352 600/479 |
| 2014/0130076 | A1* | 5/2014 | Moore | H04N 21/25883 725/19 |
| 2014/0142403 | A1* | 5/2014 | Brumback | A61B 5/14532 600/479 |
| 2014/0142964 | A1* | 5/2014 | Lang | G06Q 10/10 705/2 |
| 2014/0236847 | A1* | 8/2014 | Hamilton | G06Q 10/1093 705/319 |
| 2014/0247155 | A1* | 9/2014 | Proud | A61B 5/1118 340/870.16 |
| 2014/0258055 | A1* | 9/2014 | Wolfe | G06Q 20/321 705/30 |
| 2014/0275854 | A1* | 9/2014 | Venkatraman | A61B 5/1123 600/479 |
| 2014/0343380 | A1* | 11/2014 | Carter | A61B 5/4806 600/595 |
| 2015/0012437 | A1* | 1/2015 | Park | G06Q 20/3226 705/44 |
| 2015/0095216 | A1* | 4/2015 | Van Heerden | G06Q 30/00 705/39 |
| 2015/0112883 | A1* | 4/2015 | Orduna | H04L 67/12 705/325 |
| 2015/0227180 | A1* | 8/2015 | Rabii | G06F 1/3203 713/323 |
| 2015/0347499 | A1* | 12/2015 | Keen | G16H 20/30 707/736 |
| 2016/0026693 | A1* | 1/2016 | Dreicer | G06Q 20/405 707/769 |
| 2016/0063550 | A1* | 3/2016 | Caldwell | G06Q 30/0269 705/14.53 |
| 2016/0173359 | A1* | 6/2016 | Brenner | G16Z 99/00 709/224 |
| 2016/0183029 | A1* | 6/2016 | Kang | H04W 4/80 455/41.2 |
| 2016/0364993 | A1* | 12/2016 | Chetlur | G09B 5/06 |
| 2017/0032375 | A1* | 2/2017 | Van Os | G06Q 20/36 |
| 2017/0129426 | A1* | 5/2017 | Smith | G07C 5/0825 |
| 2017/0293740 | A1* | 10/2017 | Xing | G10L 15/18 |
| 2017/0319148 | A1* | 11/2017 | Shahin | A61B 5/02055 |
| 2018/0357887 | A1* | 12/2018 | Geyer | G08B 25/016 |
| 2018/0365382 | A1* | 12/2018 | Bhuiya | G16H 40/63 |
| 2021/0134434 | A1* | 5/2021 | Riley | G16H 20/60 |

OTHER PUBLICATIONS

Ohshige, K., Kawakami, C., Mizushima, S. et al. Evaluation of an algorithm for estimating a patient's life threat risk from an ambulance call. BMC Emerg Med 9, 21 (2009). (ER). (Year: 2009).*

* cited by examiner

APPARATUSES AND METHODS FOR RESPONSIVE FINANCIAL TRANSACTIONS

TECHNOLOGICAL FIELD

Example embodiments of the present disclosure relate generally to financial transactions and, more particularly, to responsive financial transactions.

BACKGROUND

Financial institutions often have access to a large amount of user data, user account data, and the like generated in the course of user interactions with these institutions. This data may be utilized by these entities to suggest financial products and/or financial transactions to their customers. Financial institutions may also leverage new sources of user data in an attempt to derive further insights regarding their customers.

BRIEF SUMMARY

As described above, financial institutions have traditionally had access to a large amount of user data from user accounts, transactions, mortgage information, and the like, generated by user interactions with these institutions. Financial institutions have also recently turned to previously-untapped data sources such as social media data to derive further insights about their customers. In the context of health related events and/or transactions, however, financial institutions often struggle to provide timely assistance to users. In particular, users may experience health related emergencies that not only prevent their ability to access systems of the financial institution, but further require dynamic adjustment of their financial position to properly respond to these emergencies.

To solve these issues and others, example implementations of embodiments of the present disclosure may utilize the advent of new wearable technology (e.g., smartwatches, smart glasses, etc.) as a new source of user data to provide insights associated with characteristics (e.g., heartrate, temperature, relative motion, etc.) of the user. In operation, embodiments of the present application may monitor device data associated with a user (e.g., heart rate, blood pressure, and/or other biometric data) to identify potential critical events (e.g., health issues and/or medical emergencies) associated with the user. These embodiments may further acquire financial profile data of the user (e.g., account information, transfer instructions, etc.) to perform financial actions or the like in response to this emergency. In this way, the inventors have identified that the advent of emerging computing technologies have created a new opportunity for solutions for responsive transactions which were historically unavailable. In doing so, such example implementations confront and solve at least two technical challenges: (1) they, in real time, identify potential critical events associated with a user, and (2) they dynamically adjust a user's financial position in response to determined critical events.

As such, apparatuses, methods, and computer program products are provided for responsive transactions. With reference to an example method, the example method may include receiving, via a computing device, device data of a first user device, wherein the first user device is associated with a first user. The method may further include determining, via device analysis circuitry of the computing device, a critical event of the first user based upon the device data. The method may further include acquiring, via parameter retrieval circuitry of the computing device, financial profile parameters of a first user profile associated with the first user. The method may also include generating, via preparation circuitry of the computing device, a responsive financial transaction based upon the critical event and the financial profile parameters.

In some embodiments, the method may further include effectuating, via disbursement circuitry of the computing device, the responsive financial transaction.

In some embodiments, the method may further include generating, via the computing device, a user notification comprising the responsive financial transaction.

In some embodiments, determining the critical event may further include receiving device data indicative of one or more characteristics of the first user associated with the first user device. In such an embodiment, the method may further include determining, via the device analysis circuitry, if at least one characteristic of the device data satisfies a corresponding characteristic threshold. In an instance in which at least one characteristic satisfies the corresponding characteristic threshold, the method may include determining, via the device analysis circuitry of the computing device, a critical event of the first user.

In some embodiments, the method may include receiving, via a computing device, device data of a second user device that is associated with the first user. In such an embodiment, the method may include determining, via device analysis circuitry of the computing device, the critical event of the first user based upon the device data of the first user device and the second user device.

In some embodiments, the method may include generating the responsive financial transaction by staging, via the preparation circuitry, one or more operations of the responsive financial transaction.

In other embodiments, the method may include generating the responsive financial transaction further by effectuating, via disbursement circuitry of the computing device, the responsive financial transaction.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings. The components illustrated in the figures may or may not be present in certain embodiments described herein. Some embodiments may include fewer (or more) components than those shown in the figures.

DETAILED DESCRIPTION

Figure 1:
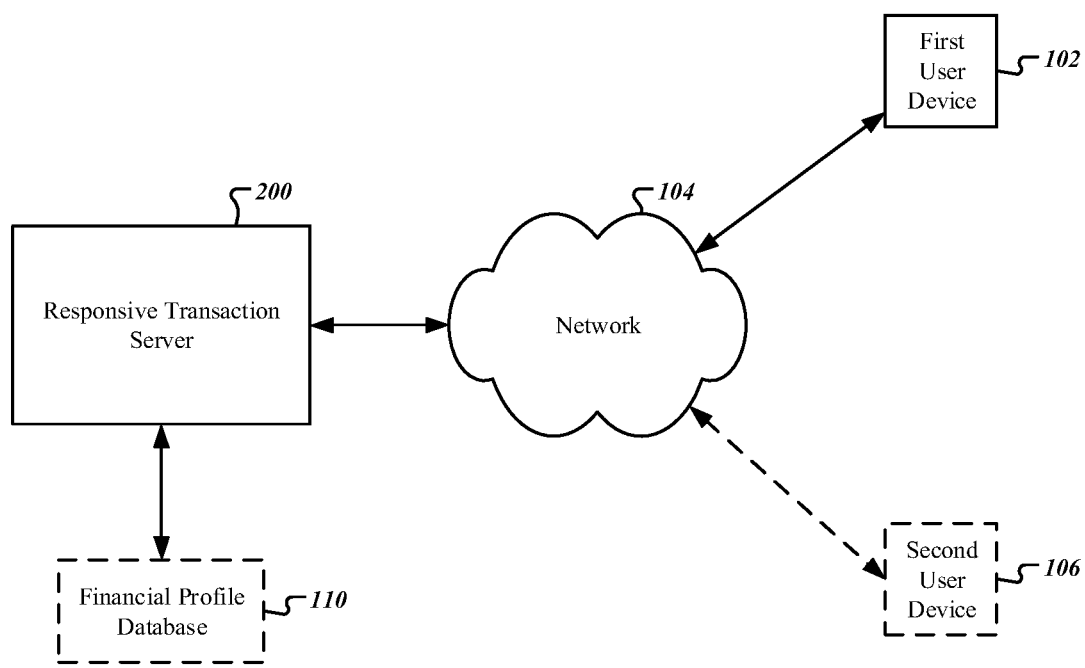
FIG. 1 illustrates a system diagram including devices that may be involved in some example embodiments described herein.

Some embodiments of the present disclosure will now be described more fully hereinafter with reference to the accompanying drawings, in which some, but not all embodiments are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout. As used herein, the description may refer to a responsive transaction server as an example "apparatus." However, elements of the apparatus described herein may be equally applicable to the claimed method and computer program product. Thus, use of any such terms should not be taken to limit the spirit and scope of embodiments of the present disclosure.

Definition of Terms

As used herein, the terms "data," "content," "information," "electronic information," "signal," "command," and similar terms may be used interchangeably to refer to data capable of being transmitted, received, and/or stored in accordance with embodiments of the present disclosure. Thus, use of any such terms should not be taken to limit the spirit or scope of embodiments of the present disclosure. Further, where a first computing device is described herein to receive data from a second computing device, it will be appreciated that the data may be received directly from the second computing device or may be received indirectly via one or more intermediary computing devices, such as, for example, one or more servers, relays, routers, network access points, base stations, hosts, and/or the like, sometimes referred to herein as a "network." Similarly, where a first computing device is described herein as sending data to a second computing device, it will be appreciated that the data may be sent directly to the second computing device or may be sent indirectly via one or more intermediary computing devices, such as, for example, one or more servers, remote servers, cloud-based servers (e.g., cloud utilities), relays, routers, network access points, base stations, hosts, and/or the like.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the word "example" is used herein to mean "serving as an example, instance, or illustration." Any implementation described herein as "example" is not necessarily to be construed as preferred or advantageous over other implementations.

As used herein, the terms "user profile" and "first user profile" refer to a collection of settings, configurations, identifiers, data, and information associated with a specific user. A user profile configured in accordance with the present disclosure may be accessible by one or more of the software applications that are supported by the responsive transaction server and, thus, may include application-specific preferences, settings, configurations, data, and information. In some example embodiments, a first user profile may include account information, preferences, transaction instructions, and/or the like associated with the first user as described hereafter.

As used herein, the terms "user device," "first user device," "second user device," and the like refer to computer hardware and/or software that is configured to access a service made available by the responsive transaction server and, among various other functions, is configured to directly, or indirectly, transmit and receive at least device data. Example user devices may include a smartphone, a tablet computer, a laptop computer, a wearable device (e.g., smart glasses, smartwatch, or the like), and the like. In some embodiments, a user device may include a "smart device" that is equipped with chip of other electronic device that is configured to communicate with the responsive transaction server via Bluetooth, NFC, Wi-Fi, 3G, 4G, 5G, RFID protocols, and the like. By way of a particular example, a first user device may be a smartwatch and a second user device may be smart glasses, where each user device is equipped with a Wi-Fi radio that is configured to communicate with a Wi-Fi access point that is in communication with the a server (e.g., a responsive transaction server of the present disclosure) via a network.

As used herein, the term "financial profile database" refers to a data structure or repository for storing user profiles and associated financial profile parameters. Similarly, the financial profile parameters of the financial profile database may refer to data generated by or associated with a plurality of users or user devices and stored in a user profile for the particular user. By way of example, the financial profile parameters may include user data regarding the race, gender, income, geographic location, employment, birthdate, social security number, etc. of respective users. Furthermore, the financial profile parameters may include instructions for performing financial transactions associated with one or more accounts of the user. By way of example, the financial profile parameters of a first user profile associated with a first user may include instructions that, in response to determining a health-related emergency (e.g., critical event), effectuate financial transactions associated with an account of the first user. The financial profile database may be accessible by one or more software applications of the responsive transaction server 200.

As used herein, the term "computer-readable medium" refers to non-transitory storage hardware, non-transitory storage device or non-transitory computer system memory that may be accessed by a controller, a microcontroller, a computational system or a module of a computational system to encode thereon computer-executable instructions or software programs. A non-transitory "computer-readable medium" may be accessed by a computational system or a module of a computational system to retrieve and/or execute the computer-executable instructions or software programs encoded on the medium. Exemplary non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM), and the like.

Having set forth a series of definitions called-upon throughout this application, an example system architecture and example apparatus is described below for implementing example embodiments and features of the present disclosure.

Device Architecture and Example Apparatus

With reference to FIG. 1, an example system 100 is illustrated with an apparatus (e.g., a responsive transaction server 200) communicably connected via a network 104 to a first user device 102 and, in some embodiments, a second user device 106. The example system 100 may also include a financial profile database 110 that may be hosted by the responsive transaction server 200 or otherwise hosted by devices in communication with the responsive transaction server 200. Although illustrated connected to the responsive transaction server 200 via a network 104, the present disclosure contemplates that one or more of the first user device 102 and/or the second user device 106 may be hosted and/or stored by the responsive transaction server 200.

The responsive transaction server 200 may include circuitry, networked processors, or the like configured to perform some or all of the apparatus-based (e.g., responsive transaction server-based) processes described herein, and may be any suitable network server and/or other type of processing device. In this regard, responsive transaction server 200 may be embodied by any of a variety of devices. For example, the responsive transaction server 200 may be configured to receive/transmit data and may include any of a variety of fixed terminals, such as a server, desktop, or kiosk, or it may comprise any of a variety of mobile terminals, such as a portable digital assistant (PDA), mobile telephone, smartphone, laptop computer, tablet computer, or in some embodiments, a peripheral device that connects to one or more fixed or mobile terminals. Example embodiments contemplated herein may have various form factors and designs but will nevertheless include at least the components illustrated in FIG. 2 and described in connection therewith. In some embodiments, the responsive transaction server 200 may be located remotely from the first user device 102, the second user device 106, and/or financial profile database 110, although in other embodiments, the responsive transaction server 200 may comprise the first user device 102, the second user device 106, and/or the financial profile database 110. The responsive transaction server 200 may, in some embodiments, comprise several servers or computing devices performing interconnected and/or distributed functions. Despite the many arrangements contemplated herein, the responsive transaction server 200 is shown and described herein as a single computing device to avoid unnecessarily overcomplicating the disclosure.

The network 104 may include one or more wired and/or wireless communication networks including, for example, a wired or wireless local area network (LAN), personal area network (PAN), metropolitan area network (MAN), wide area network (WAN), or the like, as well as any hardware, software and/or firmware for implementing the one or more networks (e.g., network routers, switches, hubs, etc.). For example, the network 104 may include a cellular telephone, mobile broadband, long term evolution (LTE), GSM/EDGE, UMTS/HSPA, IEEE 802.11, IEEE 802.16, IEEE 802.20, Wi-Fi, dial-up, and/or WiMAX network. Furthermore, the network 104 may include a public network, such as the Internet, a private network, such as an intranet, or combinations thereof, and may utilize a variety of networking protocols now available or later developed including, but not limited to TCP/IP based networking protocols.

The first user device 102 may be associated with a first user and first user profile. Additional user devices (i.e., second user device 106) may be also be associated with the first user and the first user profile. Although two user devices are shown, the example system 100 may include any number of user devices that may be associated with various other users and/or user profiles. The first user device 102 and the second user device 106 may be cellular telephones (including smartphones and/or other types of mobile telephones), laptops, tablets, electronic readers, e-book devices, media devices, wearables, smart glasses, smartwatches, or any combination of the above. By way of example, the first user device 102 may include a smartwatch that includes a plurality of sensors (e.g., heartrate monitors, accelerometers, gyroscopes, thermometers, and/or the like) configured to generate device data indicative of one or more characteristics of the first user associated with the first user device 102. By way of further example, the second user device 106 may include a mobile device that includes a plurality of sensors (e.g., heartrate monitors, accelerometers, gyroscopes, thermometers, and/or the like) configured to generate device data indicative of one or more characteristics of the first user associated with the second user device 106.

The financial profile database 110 may be stored by any suitable storage device configured to store some or all of the information described herein (e.g., memory 204 of the responsive transaction server 200 or a separate memory system separate from the responsive transaction server 200, such as one or more database systems, backend data servers, network databases, cloud storage devices, or the like provided by another device (e.g., online application or $3^{rd}$ party provider) or the first or second user devices 102, 106). The financial profile database 110 may comprise data received from the responsive transaction server 200 (e.g., via a memory 204 and/or processor(s) 202), the first user device 102, and/or the second user device 106, and the corresponding storage device may thus store this data.

Figure 2:
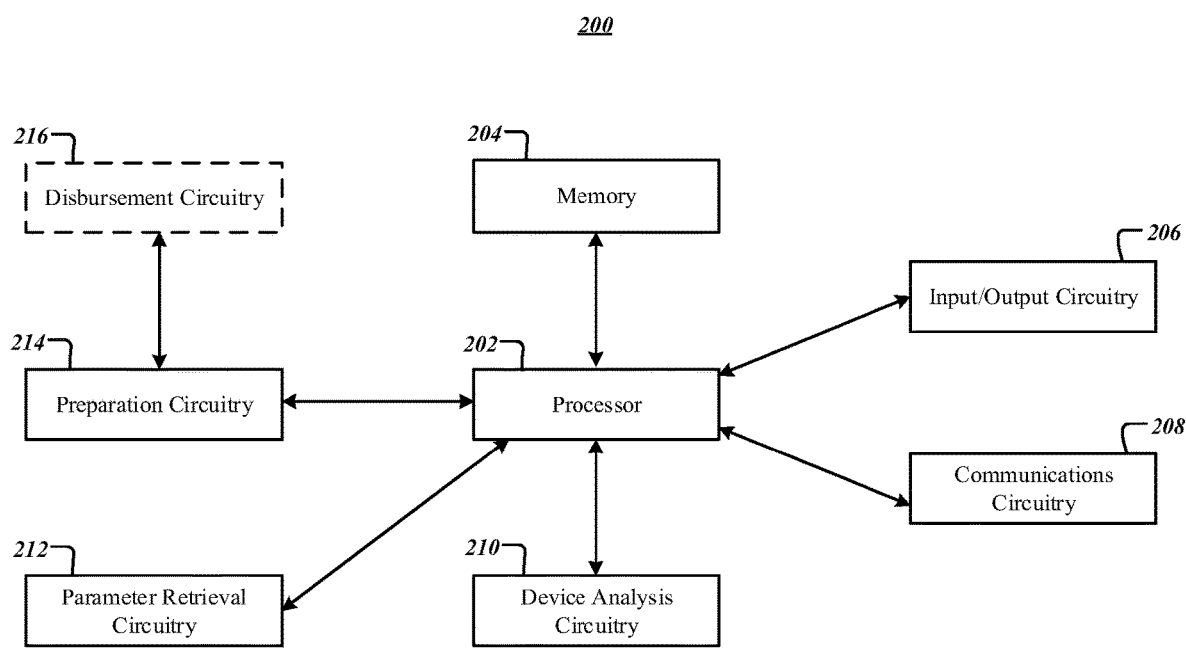
FIG. 2 illustrates a schematic block diagram of example circuitry that may perform various operations, in accordance with some example embodiments described herein.

As illustrated in FIG. 2, the responsive transaction server 200 may include a processor 202, a memory 204, communications circuitry 208, and input/output circuitry 206. Moreover, the responsive transaction server 200 may include device analysis circuitry 210, parameter retrieval circuitry 212, preparation circuitry 214, and, in some embodiments, disbursement circuitry 216. The responsive transaction server 200 may be configured to execute the operations described below in connection with FIGS. 3-5. Although components 202-216 are described in some cases using functional language, it should be understood that the particular implementations necessarily include the use of particular hardware. It should also be understood that certain of these components 202-216 may include similar or common hardware. For example, two sets of circuitry may both leverage use of the same processor 202, memory 204, communications circuitry 208, or the like to perform their associated functions, such that duplicate hardware is not required for each set of circuitry. The use of the term "circuitry" as used herein includes particular hardware configured to perform the functions associated with respective circuitry described herein. As described in the example above, in some embodiments, various elements or components of the circuitry of the responsive transaction server 200 may be housed within the first user device 102, and/or the second user device 106. It will be understood in this regard that some of the components described in connection with the responsive transaction server 200 may be housed within one of these devices, while other components are housed within another of these devices, or by yet another device not expressly illustrated in FIG. 1.

Of course, while the term "circuitry" should be understood broadly to include hardware, in some embodiments, the term "circuitry" may also include software for configuring the hardware. For example, although "circuitry" may include processing circuitry, storage media, network interfaces, input/output devices, and the like, other elements of the responsive transaction server 200 may provide or supplement the functionality of particular circuitry.

In some embodiments, the processor 202 (and/or co-processor or any other processing circuitry assisting or otherwise associated with the processor) may be in communication with the memory 204 via a bus for passing information among components of the responsive transaction server 200. The memory 204 may be non-transitory and may include, for example, one or more volatile and/or non-volatile memories. In other words, for example, the memory may be an electronic storage device (e.g., a non-transitory computer readable storage medium). The memory 204 may be configured to store information, data, content, applications, instructions, or the like, for enabling the responsive transaction server 200 to carry out various functions in accordance with example embodiments of the present disclosure.

The processor 202 may be embodied in a number of different ways and may, for example, include one or more processing devices configured to perform independently. Additionally, or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the responsive transaction server, and/or remote or "cloud" processors.

In an example embodiment, the processor 202 may be configured to execute instructions stored in the memory 204 or otherwise accessible to the processor 202. Alternatively, or additionally, the processor 202 may be configured to execute hard-coded functionality. As such, whether configured by hardware or by a combination of hardware with software, the processor 202 may represent an entity (e.g., physically embodied in circuitry) capable of performing operations according to an embodiment of the present disclosure while configured accordingly. Alternatively, as another example, when the processor 202 is embodied as an executor of software instructions, the instructions may specifically configure the processor 202 to perform the algorithms and/or operations described herein when the instructions are executed.

The responsive transaction server 200 further includes input/output circuitry 206 that may, in turn, be in communication with processor 202 to provide output to a user and to receive input from a user, user device, or another source. In this regard, the input/output circuitry 206 may comprise a display that may be manipulated by a mobile application. In some embodiments, the input/output circuitry 206 may also include additional functionality such as a keyboard, a mouse, a joystick, a touch screen, touch areas, soft keys, a microphone, a speaker, or other input/output mechanisms. The processor 202 and/or user interface circuitry comprising the processor 202 may be configured to control one or more functions of a display through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the responsive transaction server 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally, or alternatively, the communication interface may include the circuitry for interacting with the antenna(s) to cause transmission of signals via the antenna(s) or to handle receipt of signals received via the antenna(s). These signals may be transmitted by the responsive transaction server 200 using any of a number of wireless personal area network (PAN) technologies, such as Bluetooth® v1.0 through v3.0, Bluetooth Low Energy (BLE), infrared wireless (e.g., IrDA), ultra-wideband (UWB), induction wireless transmission, or the like. In addition, it should be understood that these signals may be transmitted using Wi-Fi, Near Field Communications (NFC), Worldwide Interoperability for Microwave Access (WiMAX) or other proximity-based communications protocols.

The device analysis circuitry 210 includes hardware components designed to determine critical events of the first user based upon device data. The device analysis circuitry 210 may further include hardware components for determining if one or more characteristics of device data satisfies one or more corresponding characteristic thresholds. The device analysis circuitry 210 may utilize processing circuitry, such as the processor 202, to perform its corresponding operations, and may utilize memory 204 to store collected information.

The parameter retrieval circuitry 212 includes hardware components designed to acquire financial profile parameters of a first user profile associated with the first user. In some embodiments, the parameter retrieval circuitry 212 may be configured to query the financial profile database 110 to acquire one or more financial profile parameters. The parameter retrieval circuitry 212 may utilize processing circuitry, such as the processor 202, to perform its corresponding operations, and may utilize memory 204 to store collected information.

The preparation circuitry 214 includes hardware components designed to generate a responsive financial transaction based upon a determined critical event and financial profile parameters of a first user. In some embodiments, the preparation circuitry 214 may be configured to stage one or more operations of the responsive financial transaction. In some embodiments, the preparation circuitry 214 may include disbursement circuitry 216 designed to effectuate the responsive financial transaction. The preparation circuitry 214 and/or disbursement circuitry 216 may utilize processing circuitry, such as the processor 202, to perform their corresponding operations, and may utilize memory 204 to store collected information.

It should also be appreciated that, in some embodiments, the device analysis circuitry 210, parameter retrieval circuitry 212, preparation circuitry 214, and/or disbursement circuitry 216 may include a separate processor, specially configured field programmable gate array (FPGA), or application specific interface circuit (ASIC) to perform its corresponding functions.

In addition, computer program instructions and/or other type of code may be loaded onto a computer, processor, or other programmable responsive transaction server's circuitry to produce a machine, such that the computer, processor other programmable circuitry that execute the code on the machine create the means for implementing the various functions, including those described in connection with the components of responsive transaction server 200.

As described above and as will be appreciated based on this disclosure, embodiments of the present disclosure may be configured as systems, methods, mobile devices, and the like. Accordingly, embodiments may comprise various means including entirely of hardware or any combination of software with hardware. Furthermore, embodiments may take the form of a computer program product comprising instructions stored on at least one non-transitory computer-readable storage medium (e.g., computer software stored on a hardware device). Any suitable computer-readable storage medium may be utilized including non-transitory hard disks, CD-ROMs, flash memory, optical storage devices, or magnetic storage devices.

Example Operations for Responsive Transactions

Figure 3:
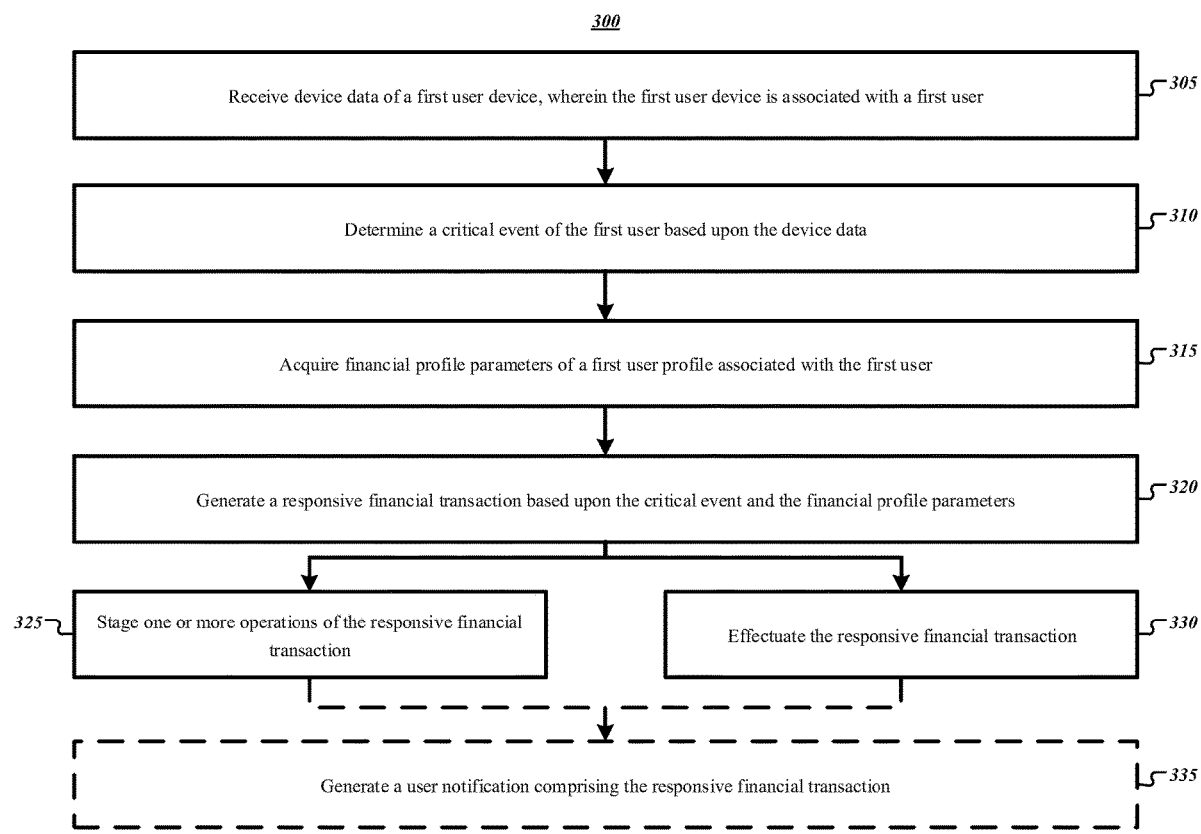
FIG. 3 illustrates an example flowchart for responsive financial transactions, in accordance with some example embodiments described herein.

FIG. 3 illustrates a flowchart containing a series of operations for improved responsive transactions. The operations illustrated in FIG. 3 may, for example, be performed by, with the assistance of, and/or under the control of an apparatus (e.g., responsive transaction server 200), as described above. In this regard, performance of the operations may invoke one or more of processor 202, memory 204, input/output circuitry 206, communications circuitry 208, device analysis circuitry 210, parameter retrieval circuitry 212, preparation circuitry 214, and/or disbursement circuitry 216.

As shown in operation 305, the apparatus (e.g., responsive transaction server 200) includes means, such as input/output circuitry 206, communications circuitry 208, or the like, for receiving device data of a first user device 102, wherein the first user device 102 is associated with a first user. As described above, the first user device 102 may be configured to generate device data indicative of one or more characteristics of the first user. By way of continued example, the first user device 102 may be a smartwatch worn by the first user and configured to, via a plurality of sensors (e.g., heartrate monitor, accelerometer, gyroscope, thermometer, and/or the like), generate device data regarding the heartrate, position, movement, temperature, etc. of the first user. Although described herein with reference to an embodiment in which the first user device 102 is a smartwatch, the present disclosure contemplates that any user device (e.g., laptop, mobile phone, smart glasses, etc.) configured to generate device data of any type may be used in conjunction with the responsive transaction server 200 and operations described herein.

In some embodiments, the device data received at operation 305 may be transmitted by the first user device 102 in response to a request by the responsive transaction server 200. As described hereafter, in some embodiments, the device data of the first user device 102 may be transmitted to the responsive transaction server 200 in response to determining a critical event of the first user. In other embodiments, however, the first user device 102 may periodically or automatically transmit device data of the first user device 102 to the responsive transaction server 200 at Block 305. Similarly, in other embodiments, the responsive transaction server 200 may periodically request device data of the first user device 102 at Block 305.

Thereafter, as shown in operation 310, the apparatus (e.g., responsive transaction server 200) includes means, such as input/output circuitry 206, communication circuitry 208, device analysis circuitry 210 or the like, for determining a critical event of the first user based upon the device data. As described hereafter with reference to FIGS. 4 and 5, the device analysis circuitry 210 may be configured to, in response to device data received at operation 305, determine a critical event (e.g., health related event, medical emergency, or the like) of the first user. By way of example, the responsive transaction server 200 may receive device data at operation 305 from a smart watch (e.g., first user device 102) comprising heart rate data. At operation 310, the responsive transaction server 200 may determine a critical event of the first user in an instance in which the heart rate data satisfies a heart rate related threshold. Said differently, the device analysis circuitry 210 may analyze the heart rate data received at operation 305 (e.g., device data) and determine that the heart rate data satisfies one or more thresholds associated with a medical emergency (e.g., a heartbeat that is too low or too high).

Although described herein with reference to device data comprising heartrate data, the present disclosure contemplates that the device analysis circuitry 210 may analyze device data of any type in order to determine a critical event. By way of example, the responsive transaction server 200 may receive device data at operation 305 from a first user device 102 comprising acceleration and positional data. At operation 310, the responsive transaction server 200 may determine a critical event of the first user in an instance in which the acceleration and positional data satisfies a motion related threshold. Said differently, the device analysis circuitry 210 may analyze the acceleration and positional received at operation 305 (e.g., device data) and determine that this data satisfies one or more thresholds associated with a medical emergency (e.g., a fall, car accident, etc.). By way of an additional example, the responsive transaction server 200 may receive device data at operation 305 from a first user device 102 comprising temperature and/or pressure data. At operation 310, the responsive transaction server 200 may determine a critical event of the first user in an instance in which the temperature and/or pressure satisfies a temperature or pressure related threshold. Said differently, the device analysis circuitry 210 may analyze the temperature and pressure received at operation 305 (e.g., device data) and determine that this data satisfies one or more thresholds associated with a medical emergency (e.g., fire, hurricane, or other natural disaster).

Thereafter, as shown in operation 315, the apparatus (e.g., responsive transaction server 200) includes means, such as processor 202, parameter retrieval circuitry 212, or the like, for acquiring financial profile parameters of a first user profile associated with the first user. As described above, the first user and first user device 102 may be associated with a first user profile. The first user profile may include user data (e.g., username, password, age, gender, social security number, or the like) that identifies the first user while also including account information, preferences, and/or transaction instructions. In some embodiments, the first user profile may be generated in response to one or more user inputs of the first user. By way of example, the first user may provide user account information, transaction instructions, account preferences, and/or the like as part of an initial set up. In other embodiments, the first user profile may be generated by the responsive transaction server 200 based upon one or more interactions by the first user (e.g., first user device 102) and the responsive transaction server 200. By way of example, the parameter retrieval circuitry 212 may be configured to monitor user actions (e.g., account inputs, prior user transactions, etc.) in order to determine (e.g., via machine learning techniques or the like) one or more account preferences or transaction instructions for the first user profile.

In some embodiments, the responsive transaction server 200 or the first user device 102 may store the first user profile. In other embodiments, the financial profile database 110 may store the first user profile amongst a plurality of other user profiles associated with respective users. The financial profile database 110 may be iteratively updated based upon one or more user inputs (e.g., modifying account settings, preferences, and/or transaction instructions) or determinations by the parameter retrieval circuitry 212. In such an embodiment, the responsive transaction server 200 may query the financial profile database 110 to acquire financial profile parameters of the first user profile at operation 315.

With continued reference to operation 315, the financial profile parameters of the first user profile may operate to define operation of the user's finances generally, but also instances in which critical events are determined. By way of example, the first user may generally define that he or she prefers a particular risk tolerance when investing, a certain distribution of funds between accounts, and/or the like. Furthermore, the first user may define (or the parameter retrieval circuitry 212 may iteratively determine) transaction instructions when critical events are determined. For example, the financial profile parameters of the first user profile may provide instructions to, in an instance in which a critical event regarding the first user's heath is determined as described above, transfer funds from an investment account to a checking account, withdraw funds from a health savings account (HSA), generate a quick response (QR) code containing financial information of the first user, and/or the like. By way of an additional example, the financial profile parameters of the first user profile may provide instructions to, in an instance in which a critical event regarding the first user's automobile is determined as described above (e.g., a car accident), transfer funds to an account associated with an automobile repair shop, generate a deductible payment for an associated insurance policy, and/or the like. The present disclosure contemplates that the financial profile parameters of the first user profile may include instructions configured to stage or effectuate a responsive financial transaction as described herein.

In some embodiments, as shown in operation 320, the apparatus (e.g., responsive transaction server 200) includes means, such as processor 202, preparation circuitry 214, or the like, for generating a responsive financial transaction based upon the critical event and the financial profile parameters. As described herein, the responsive transaction server 200 may be uniquely positioned as part of the infrastructure of a financial institution such that the server 200 may stage and/or complete financial transactions in response to a determined critical event. Said differently, the responsive transaction server 200 described herein may operate to efficiently stage and complete financial transactions in instances in which a user (e.g., first user) is unavailable or incapacitated and when timely responses are of critical importance.

With continued reference to FIG. 3, the preparation circuitry 214 may, at operation 320, generate a responsive financial transaction in accordance with the financial profile parameters of the first user profile for the determined critical event. By way of continued example, the financial profile parameters of the first user profile may include instructions to complete a financial transaction (as described with reference to operation 330) that withdraws funds from the first user's health savings account (HSA) in an instance in which the critical event determined at operation 310 corresponds to a health related emergency. Thereafter, as shown in operation 330, the apparatus (e.g., responsive transaction server 200) includes means, such as processor 202, disbursement circuitry 216, or the like, for effectuating the responsive financial transaction as described above. In such an embodiment, generation of the responsive financial transaction at operation 320 may include performance of operation 300 automatically. Said differently, the financial profile parameters of the first user profile may indicate that an automatic (e.g., without further review and/or approval by the first user) financial transaction should occur, and the disbursement circuitry 216 may effectuate this responsive financial transaction.

In other embodiments, as shown in operation 325, the apparatus (e.g., responsive transaction server 200) includes means, such as processor 202, preparation circuitry 214, or the like, for staging one or more operations of the responsive financial transaction. In such an embodiment, the financial profile parameters of the first user profile may include instructions to stage or otherwise prepare one or more operations of the responsive financial transaction. By way of example, the first user may, prior to completing the transaction, review the responsive financial transaction. In order to facilitate effective completion and expedited processing of the responsive financial transaction, the preparation circuitry 214 may prepare transaction documentation, apportion account funds, and/or the like. The present disclosure contemplates that the preparation circuitry operation 325 may stage any number of operations so as to facilitate future transactions of the first user based upon the intended application of the responsive transaction server 200.

In some embodiments, in response to operation 325 or 330, the apparatus (e.g., responsive transaction server 200) includes means, such as processor 202, communications 208, or the like, for generating a user notification comprising the responsive financial transaction. In an instance in which the disbursement circuitry 216 effectuates the responsive financial transaction at operation 330 as described above, the user notification at operation 335 may include the details, parameters, amount, or any other related account or financial information regarding the completed responsive financial transaction. In an instance in which the preparation circuitry 214 stages one or more operations of the responsive financial transaction at operation 325 as described above, the user notification at operation 335 may be actionable by the first user. Said differently, the user notification may include the details, parameters, amount, or any other related account or financial information regarding the proposed responsive financial transaction with further options for receiving approval from the first user.

Figure 4:
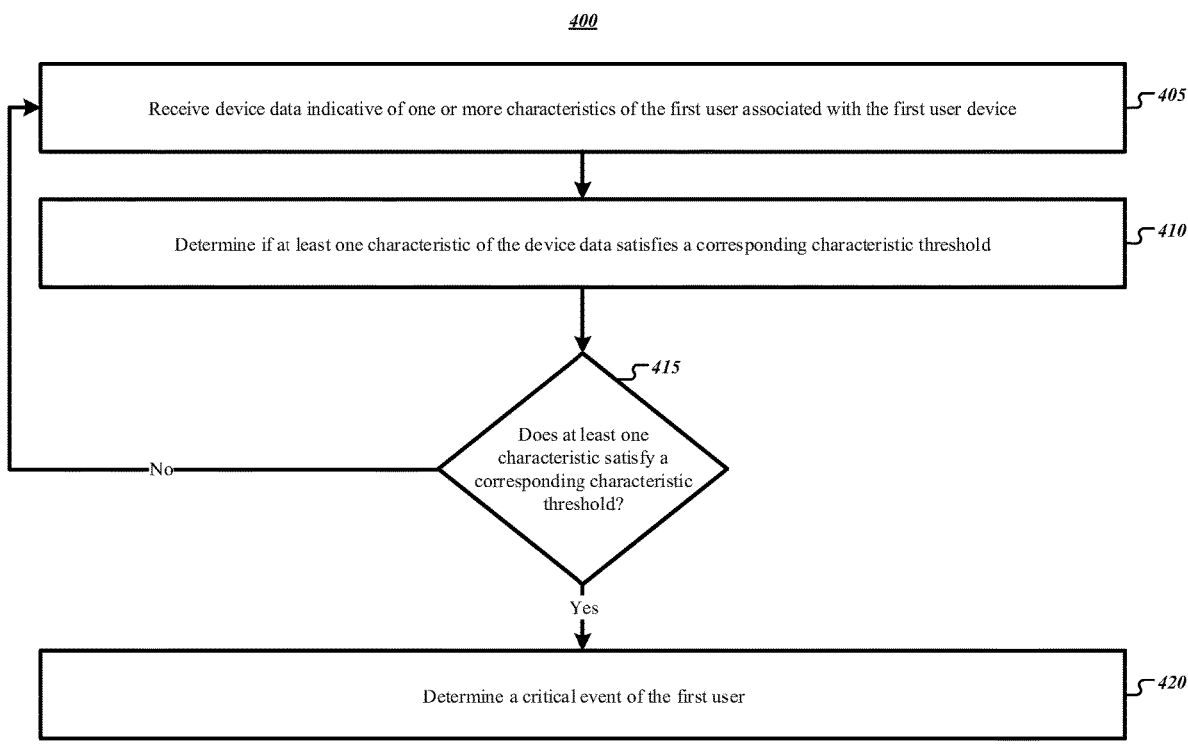
FIG. 4 illustrates an example flowchart for critical event determinations based on a first device, in accordance with some example embodiments described herein.

Turning next to FIG. 4, a flowchart is shown for critical event determinations based on a first device. The operations illustrated in FIG. 4 may, for example, be performed by, with the assistance of, and/or under the control of an apparatus (e.g., responsive transaction server 200), as described above. In this regard, performance of the operations may invoke one or more of processor 202, memory 204, input/output circuitry 206, communications circuitry 208, and/or device analysis circuitry 210.

As shown in operation 405, the apparatus (e.g., responsive transaction server 200) includes means, such as input/output circuitry 206, communications circuitry 208, parameter retrieval circuitry 212, or the like, for receiving device data indicative of one or more characteristics of the first user associated with the first user device 102. As described above with reference to operation 305, the first user device 102 may be configured to generate device data that is received by the responsive transaction server 200. The device data received by the responsive transaction server 200 at operation 405 may further be indicative of one or more characteristics of the first user.

As described above, the first user device 102 may, in some embodiments, be a smartwatch worn by the first user and configured to, via a plurality of sensors (e.g., heartrate monitor, accelerometer, gyroscope, thermometer, and/or the like), generate device data regarding the heartrate, position, movement, temperature, etc. (e.g., characteristics) of the first user. Although described with reference to an embodiment in which the first user device 102 is a smartwatch, the present disclosure contemplates that any user device (e.g., laptop, mobile phone, smart glasses, etc.) configured to generate device data of any type may be used in conjunction with the responsive transaction server 200 and operations described herein. Said differently, the device data received by the responsive transaction server 200 may be indicative of any characteristics of the first user as generated by the sensors of the first user device 102.

As shown in operations 410 and 415, the apparatus (e.g., responsive transaction server 200) includes means, such as input/output circuitry 206, communications circuitry 208, device analysis circuitry 210, or the like, for determining if at least one characteristic of the device data satisfies a corresponding characteristic threshold. By way of example, the responsive transaction server 200 may include one or more characteristic thresholds each of which is associated with a particular characteristic of the first user. These characteristic thresholds may, in some embodiments, be user inputted and/or independently determined by the responsive transaction server 200. Furthermore, each characteristic threshold may be different from other characteristic thresholds. Said differently, each characteristic may be associated with a respective threshold that may be indicative or otherwise related to the importance of the characteristic (e.g., the threshold for the heart rate of the first user may be more stringent than the threshold for the motion of the first user). Furthermore, each characteristic threshold may also be variable or otherwise dynamically adjusted based upon the intended application of the responsive transaction server 200.

With continued reference to operations 410 and 415, the characteristics may be compared with respective characteristic thresholds to determine if at least one characteristic satisfies a corresponding characteristic threshold. By way of continued example, the characteristic threshold associated with heartrate may be defined as 25 beats per minute (bpm) such that any device data associated with heart rate that exceeds 25 bpm fails to satisfy the threshold for this characteristic. Said differently, the heartrate of the first user exceeding a minimum threshold may indicate that a medical emergency based upon the first user's heartrate is not present. In an instance in which the device data of the first user device 102 indicates that the first user's heartrate fails to exceed 25 bpm, the responsive transaction server may determine that the characteristic satisfies the respective characteristic threshold at operation 410. In such an instance, the apparatus (e.g., responsive transaction server 200) may include means, such as input/output circuitry 206, device analysis circuitry 210, or the like, for determining a critical event at operation 420.

As described above, the device data generated by the first user device 102 may be periodically transmitted to the responsive transaction server 200. As shown in FIG. 4, in such an embodiment, the device analysis circuitry 210 may be configured to iteratively determine if at least one characteristic of the device data satisfies a corresponding characteristic threshold as described above. Said differently, in such an embodiment, the responsive transaction server 200 may operate to perform determinations of a critical event of the first user via circuitry housed by the server 200. In other embodiments, however, the operations described herein regarding determination of a critical event of the first user may be performed in whole or in part by the first user device 102. Said differently, in such an embodiment, the first user device 102 may compare the characteristics of the user with respective characteristic thresholds and transmit a determination of critical event to the responsive transaction server 200.

Figure 5:
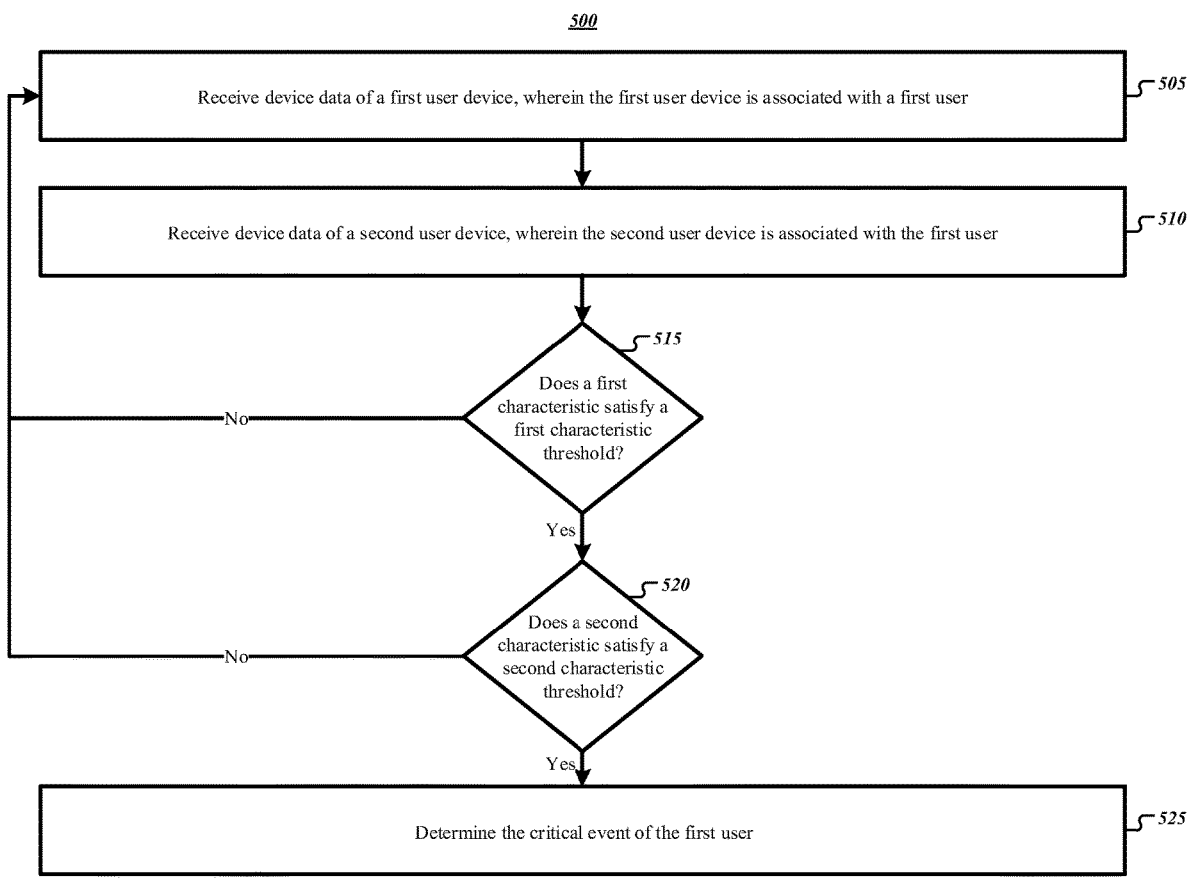
FIG. 5 illustrates an example flowchart for critical event determinations based on a first device and a second device, in accordance with some example embodiments described herein.

Turning next to FIG. 5, a flowchart is shown for critical event determinations based on a first device and a second device. The operations illustrated in FIG. 5 may, for example, be performed by, with the assistance of, and/or under the control of an apparatus (e.g., responsive transaction server 200), as described above. In this regard, performance of the operations may invoke one or more of processor 202, memory 204, input/output circuitry 206, communications circuitry 208, and/or device analysis circuitry 210. As described herein, the responsive transaction server 200 may, via the operations of FIG. 5, be configured to confirm the determination of a critical event. Said differently, the responsive transaction server 200 described herein may operate in conjunction with a second user device 106 to prevent false positives associated with characteristics of the first user device 102.

As shown in operation 505, the apparatus (e.g., responsive transaction server 200) includes means, such as input/output circuitry 206, communications circuitry 208, device analysis circuitry 210, or the like, for receiving device data indicative of one or more characteristics of the first user associated with the first user device 102. As described above, the first user device 102 may be configured to generate device data that is received by the responsive transaction server 200. The device data received by the responsive transaction server 200 at operation 505 may further be indicative of one or more characteristics of the first user. The first user device 102 may, in some embodiments, be a mobile phone of the first user and configured to, via a plurality of sensors (e.g., heartrate monitor, accelerometer, gyroscope, thermometer, and/or the like), generate device data regarding the heartrate, position, movement, temperature, etc. (e.g., characteristics) of the first user. By way of particular example, the first user device 102 may be a mobile phone of the first user configured to generate device data related to the motion (e.g., acceleration and position) of the first user.

Thereafter, as shown in operation 510, the apparatus (e.g., responsive transaction server 200) includes means, such as processor 202, communications circuitry 208, device analysis circuitry 210, or the like, for receiving device data of a second user device, wherein the second user device 106 is associated with the first user. Similar to the first user device 102, the second user device 106 may also be configured to generate device data that is received by the responsive transaction server 200. The device data received by the responsive transaction server 200 at operation 405 may similarly be indicative of one or more characteristics of the first user. The second user device 106 may, in some embodiments, be a smartwatch worn by the first user and configured to, via a plurality of sensors (e.g., heartrate monitor, accelerometer, gyroscope, thermometer, and/or the like), generate device data regarding the heartrate, position, movement, temperature, etc. (e.g., characteristics) of the first user. By way of particular example, the second user device 106 may be a smartwatch of the first user configured to generate device data related to the heartrate of the first user.

Thereafter, as shown in operation 515, the apparatus (e.g., responsive transaction server 200) includes means, such as processor 202, parameter retrieval circuitry 212, or the like, for determining if a first characteristic of the device data of the first user device 102 satisfies a first characteristic threshold. By way of continued example, in an embodiment in which the first characteristic is motion data (e.g., device data) of a mobile phone (e.g., first user device 102), the first characteristic threshold associated with motion may be defined as between 0.1 m/s$^2$ and 15.0 m/s$^2$ such that any device data associated an acceleration between 0.1 m/s$^2$ and 15.0 m/s$^2$ fails to satisfy the threshold for the first characteristic. In an instance in which the device data of the first user device 102 indicates that the acceleration of the first user device 102 is below 0.1 m/s$^2$ (e.g., stationary or constant velocity) or above 25 m/s$^2$, the responsive transaction server 200 may determine that the first characteristic satisfies the first characteristic threshold at operation 515. Given that the first user and associated first user device 102 may be stationary or moving in a vehicle (e.g., airplane, automobile, etc.), the responsive transaction server 200 may use the device data of the second device 106 to confirm whether a critical event has occurred.

Thereafter, as shown in operation 520, the apparatus (e.g., responsive transaction server 200) includes means, such as input/output circuitry 206, communications circuitry 208, parameter retrieval circuitry 212, or the like, for determining if a second characteristic of the device data of the second user device 106 satisfies a second characteristic threshold. By way of continued example, in an embodiment in which the second characteristic is heartrate data (e.g., device data) of a smartwatch (e.g., second user device 106), the second characteristic threshold associated with heartrate may be defined as 25 beats per minute (bpm) such that if the device data of the second device 106 associated with heart rate that exceeds 25 bpm, it fails to satisfy the threshold for this characteristic. In an instance in which the device data of the second user device 106 indicates that the first user's heartrate fails to exceed 25 bpm, the responsive transaction server may determine that the second characteristic satisfies the second characteristic threshold at operation 520. In such an instance, the apparatus (e.g., responsive transaction server 200) may include means, such as input/output circuitry 206, device analysis circuitry 210, or the like, for determining a critical event at operation 525.

In this way, the operation of FIG. 5 may offer redundancy to prevent false positives of critical events associated with a single user device. Said differently, if the motion data (e.g., device data) of the first user device 102 (e.g., mobile phone) indicates that the user is accelerating very fast (e.g., potentially indicative of an imminent automobile accident) or is stationary (e.g., potentially indicative of an emergency), the responsive transaction server 200 may initially determine that a critical event has occurred. However, the first user device 102 and first user may be stationary or accelerating intentionally such that a critical event is not occurring. In order to confirm whether a critical event is occurring, the device analysis circuitry 210 may compare heartrate data (e.g., device data) of a second user device 106 associated with the first user to confirm that the first user's heartrate does not indicate that a critical event is occurring.

In doing so, the embodiments of the present disclosure solve health and/or emergency related transaction issues by utilizing new wearable technology (e.g., smartwatches, smart glasses, etc.) as a new source of user data that provides insights associated with characteristics (e.g., heartrate, temperature, relative motion, etc.) of the user. The embodiments described herein monitor device data associated with a user (e.g., heart rate, blood pressure, and/or other biometric data) to identify potential critical events (e.g., health issues and/or medical emergencies) associated with the user. These embodiments further acquire financial profile data of the user (e.g., account information, transfer instructions, etc.) to perform financial actions or the like in response to this emergency. In this way, the inventors have identified that the advent of emerging computing technologies have created a new opportunity for solutions for responsive transactions which were historically unavailable. In doing so, such example implementations confront and solve at least two technical challenges: (1) they, in real time, identify potential critical events associated with a user, and (2) they dynamically adjust a user's financial position in response to determined critical events.

FIGS. 3-5 thus illustrate flowcharts describing the operation of apparatuses, methods, and computer program products according to example embodiments contemplated herein. It will be understood that each flowchart block, and combinations of flowchart blocks, may be implemented by various means, such as hardware, firmware, processor, circuitry, and/or other devices associated with execution of software including one or more computer program instructions. For example, one or more of the operations described above may be implemented by an apparatus executing computer program instructions. In this regard, the computer program instructions may be stored by a memory 204 of the responsive transaction server 200 and executed by a processor 202 of the responsive transaction server 200. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware with computer instructions.

CONCLUSION

Many modifications of the embodiments set forth herein will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for responsive transactions, the method comprising:
   receiving, via a computing device, device data of a first user device generated by one or more sensors of the first user device, wherein the first user device is associated with a first user and wherein the device data is indicative of one or more characteristics of the first user;
   determining, via device analysis circuitry of the computing device, a critical event of the first user based upon the device data, wherein the critical event is indicative of a health related emergency condition of the first user;
   acquiring, via parameter retrieval circuitry of the computing device, financial profile parameters of a first user profile associated with the first user, wherein the financial profile parameters of the first user profile comprise instructions for effectuating financial transactions associated with an account of the first user in response to health related emergency conditions of the first user; and
   generating, via preparation circuitry of the computing device, a responsive financial transaction based upon the critical event and the financial profile parameters.

2. The method according to claim 1, further comprising effectuating, via disbursement circuitry of the computing device, the responsive financial transaction.

3. The method according to claim 1, further comprising, generating, via the computing device, a user notification comprising the responsive financial transaction.

4. The method according to claim 1, wherein determining the critical event further comprises:
   receiving, via the computing device, device data indicative of one or more characteristics of the first user associated with the first user device;
   determining, via the device analysis circuitry, if at least one characteristic of the device data satisfies a corresponding characteristic threshold; and
   determining, via the device analysis circuitry of the computing device, the critical event of the first user in an instance in which at least one characteristic satisfies the corresponding characteristic threshold.

5. The method according to claim 1, further comprising:
   receiving, via the computing device, device data of a second user device, wherein the second user device is associated with the first user; and
   determining, via the device analysis circuitry of the computing device, the critical event of the first user based upon the device data of the first user device and the device data of the second user device.

6. The method according to claim 1, wherein generating the responsive financial transaction comprises staging, via the preparation circuitry, one or more operations of the responsive financial transaction.

7. The method according to claim 1, wherein generating the responsive financial transaction further comprises, effectuating, via disbursement circuitry of the computing device, the responsive financial transaction.

8. An apparatus for responsive transactions, the apparatus comprising:
   communications circuitry configured to receive device data of a first user device generated by one or more sensors of the first user device, wherein the first user device is associated with a first user and wherein the device data is indicative of one or more characteristics of the first user;
   device analysis circuitry configured to determine a critical event of the first user based upon the device data, wherein the critical event is indicative of a health related emergency condition of the first user;
   parameter retrieval circuitry configured to acquire financial profile parameters of a first user profile associated with the first user, wherein the financial profile parameters of the first user profile comprise instructions for effectuating financial transactions associated with an account of the first user in response to health related emergency conditions of the first user; and
   preparation circuitry configured to generate a responsive financial transaction based upon the critical event and the financial profile parameters.

9. The apparatus according to claim 8, further comprising disbursement circuitry configured to effectuate the responsive financial transaction.

10. The apparatus according to claim 8, wherein the communications circuitry is further configured to generate a user notification comprising the responsive financial transaction.

11. The apparatus according to claim 8, wherein the communications circuitry is further configured to receive device data indicative of one or more characteristics of the first user associated with the first user device, and wherein the device analysis circuitry is further configured to:
   determine if at least one characteristic of the device data satisfies a corresponding characteristic threshold; and
   determine the critical event of the first user in an instance in which at least one characteristic satisfies the corresponding characteristic threshold.

12. The apparatus according to claim 8, wherein the communications circuitry is further configured to receive device data of a second user device, wherein the second user device is associated with the first user, and wherein the device analysis circuitry is further configured to determine the critical event of the first user based upon the device data of the first user device and the device data of the second user device.

13. The apparatus according to claim 8, wherein the preparation circuitry is further configured to stage one or more operations of the responsive financial transaction.

14. The apparatus according to claim 13, further comprising disbursement circuitry configured to execute the one or more operations of the responsive financial transaction.

15. A non-transitory computer-readable storage medium for using an apparatus for responsive transactions, the non-transitory computer-readable storage medium storing instructions that, when executed, cause the apparatus to:
receive device data of a first user device generated by one or more sensors of the first user device, wherein the first user device is associated with a first user and wherein the device data is indicative of one or more characteristics of the first user;
determine a critical event of the first user based upon the device data, wherein the critical event is indicative of a health related emergency condition of the first user;
acquire financial profile parameters of a first user profile associated with the first user, wherein the financial profile parameters of the first user profile comprise instructions for effectuating financial transactions associated with an account of the first user in response to health related emergency conditions of the first user; and
generate a responsive financial transaction based upon the critical event and the financial profile parameters.

16. The non-transitory computer-readable storage medium according to claim 15 storing instructions that, when executed, cause the apparatus to effectuate the responsive financial transaction.

17. The non-transitory computer-readable storage medium according to claim 15 storing instructions that, when executed, cause the apparatus to generate a user notification comprising the responsive financial transaction.

18. The non-transitory computer-readable storage medium according to claim 15 storing instructions that, when executed, cause the apparatus to:
receive device data indicative of one or more characteristics of the first user associated with the first user device;
determine if at least one characteristic of the device data satisfies a corresponding characteristic threshold; and
determine the critical event of the first user in an instance in which at least one characteristic satisfies the corresponding characteristic threshold.

19. The non-transitory computer-readable storage medium according to claim 15 storing instructions that, when executed, cause the apparatus to:
receive device data of a second user device, wherein the second user device is associated with the first user; and
determine the critical event of the first user based upon the device data of the first user device and the device data of the second user device.

20. The non-transitory computer-readable storage medium according to claim 15 storing instructions that, when executed, cause the apparatus to stage one or more operations of the responsive financial transaction.

* * * * *